US012648830B2

(12) United States Patent
Redmond et al.

(10) Patent No.: US 12,648,830 B2
(45) Date of Patent: Jun. 9, 2026

(54) REFERENCE FRAME ADAPTABLE MOUNT AND METHODS

(71) Applicant: Medtronic Navigation, Inc., Louisville, CO (US)

(72) Inventors: Jerald Redmond, Germantown, TN (US); Stanley T. Palmatier, Olive Branch, MS (US); Celine Lee, Morganville, NJ (US); Dominique E. Petach, Mahwah, NJ (US); Cameron A. Pitts, Gaithersburg, MD (US); Michael F. Fernandez, Montebello, NY (US)

(73) Assignee: Medtronic Navigation, Inc., Louisville, CO (US)

( * ) Notice: Subject to any disclaimer, the term of this patent is extended or adjusted under 35 U.S.C. 154(b) by 972 days.

(21) Appl. No.: 17/651,383

(22) Filed: Feb. 16, 2022

(65) Prior Publication Data

US 2022/0265365 A1 Aug. 25, 2022

Related U.S. Application Data

(60) Provisional application No. 63/153,675, filed on Feb. 25, 2021.

(51) Int. Cl.
*A61B 34/20* (2016.01)
*A61B 90/00* (2016.01)

(52) U.S. Cl.
CPC .............. *A61B 90/39* (2016.02); *A61B 34/20* (2016.02); *A61B 2034/2055* (2016.02); *A61B 2034/2072* (2016.02); *A61B 2090/3945* (2016.02); *A61B 2090/3983* (2016.02)

(58) Field of Classification Search
CPC ......... A61B 90/35; A61B 90/50; A61B 90/57; A61B 2090/571; A61B 17/0206
See application file for complete search history.

(56) References Cited

U.S. PATENT DOCUMENTS

| | | | | |
|---|---|---|---|---|
| 4,638,799 | A | 1/1987 | Moore | |
| 5,078,140 | A * | 1/1992 | Kwoh | A61B 34/30 |
| | | | | 901/41 |
| 6,640,458 | B2 * | 11/2003 | Sawdon | B25J 15/0052 |
| | | | | 33/502 |
| 8,016,835 | B2 * | 9/2011 | Birkmeyer | A61B 90/11 |
| | | | | 606/97 |
| 10,213,262 | B2 * | 2/2019 | Shelton, IV | A61B 34/71 |

(Continued)

FOREIGN PATENT DOCUMENTS

WO 2016201292 A1 12/2016

OTHER PUBLICATIONS

"Walimex Pro 28cm Magic Arm for DSLR Rigs and Dollies", amazon.de, p. 1, XP002806814, Retrieved from URL: https://www.amazon.de/Walimex-DSLR-Gelenkarm-Auslegearm-Videostative-Aufnahmetische/dp/B008BEPHJ6/ref=sr_1_10?_mk_de_DE=%c3%85M%C3%85%C5%BD%C3%95%C3%91&crid=2UGTERRTEMK41&keywords=WALIMEX+PRO+DSLR&qid=1655275354&sprefix=walimex+pro+dslr, aps, 109&sr=8-10, retrieved on Jun. 15, 2022, the whole document.

*Primary Examiner* — Anu Ramana

(57) ABSTRACT

Devices and methods used to mount a patient reference frame for image-guided surgery are disclosed. The devices include an adaptable mount having first, second, and third joints that provide up to five axes of movement. One or more of the joints include discrete positions detectable by a visual tracking device to allow re-registration of the patient reference frame.

19 Claims, 8 Drawing Sheets

(56)  References Cited

U.S. PATENT DOCUMENTS

| | | | | |
|---|---|---|---|---|
| 11,060,836 B2 * | 7/2021 | Hunter | ................. | G01B 5/0004 |
| 11,453,118 B2 * | 9/2022 | Brogardh | ............... | B25J 9/0072 |
| 11,731,265 B2 * | 8/2023 | Brogardh | ................. | B25J 9/106 |
| | | | | 700/245 |
| 11,744,661 B2 * | 9/2023 | Beckman | ............... | A61B 34/37 |
| | | | | 606/130 |
| 11,771,509 B2 * | 10/2023 | Beckman | ........... | F16H 57/0025 |
| | | | | 606/1 |
| 11,865,711 B2 * | 1/2024 | Brogardh | ................. | B25J 9/042 |
| 11,897,127 B2 * | 2/2024 | DiMaio | .................. | A61B 90/94 |
| 2003/0177656 A1 * | 9/2003 | Sawdon | ............. | B25J 15/0052 |
| | | | | 33/645 |
| 2005/0273132 A1 * | 12/2005 | Shluzas | ............. | A61B 17/7007 |
| | | | | 606/198 |
| 2009/0149848 A1 * | 6/2009 | Werneth | ................. | A61B 18/18 |
| | | | | 606/41 |
| 2012/0078061 A1 * | 3/2012 | Calafiore | ........... | A61B 17/0483 |
| | | | | 600/229 |
| 2017/0072559 A1 * | 3/2017 | Parks | .................... | B25J 18/007 |

* cited by examiner

REFERENCE FRAME ADAPTABLE MOUNT AND METHODS

RELATED APPLICATIONS

This application claims priority to U.S. Provisional Application No. 63/153,675, filed on Feb. 25, 2021 and titled "Reference Frame Adaptable Mount And Methods" which is hereby incorporated by reference in its entirety.

TECHNICAL FIELD

The present disclosure relates generally to devices used in image-guided surgery. More specifically, the present disclosure relates to devices used to mount a patient reference frame used in image-guided surgery.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
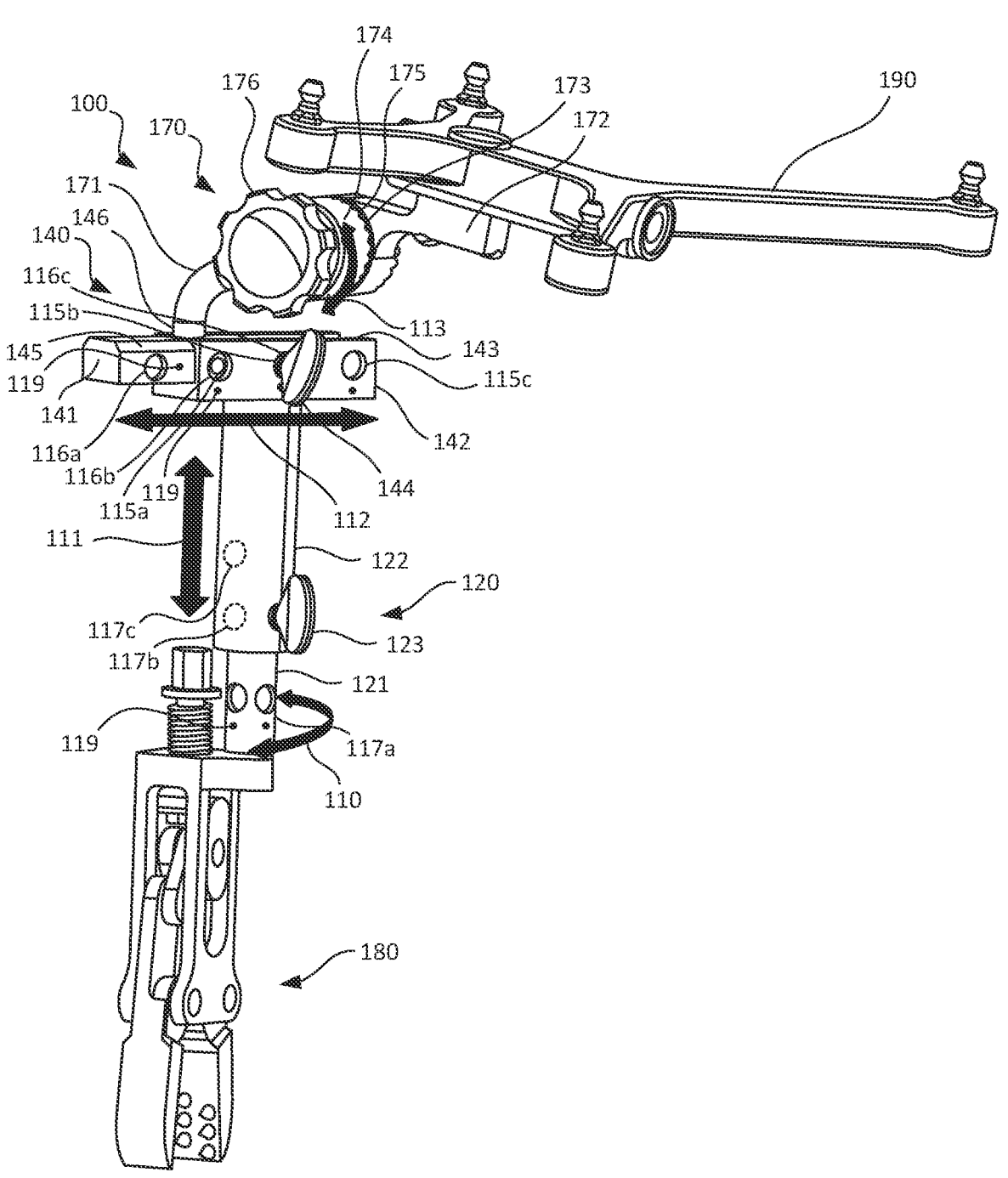
FIG. 1 is a perspective view of an embodiment of a reference frame mount.

In certain instances, image-guided surgery of the spine utilizes three-dimensional (3D) image data from computed tomography (CT) or 3D fluoroscopy to create a virtual map of the patient's anatomy that can be registered to the patient's physical position. This virtual map can allow for real-time localization of instruments and implants relative to the patient's anatomy in 3D space, utilizing computer systems equipped with tracking technologies and software. The image data can be acquired several days before the surgery or just prior to the surgery, with both manual and automatic registration techniques available for registering the image data to the patient. In some embodiments, a component of automatic registration involves use of a reference frame, where a tracking instrument or imaging phantom is attached to the patient during collection of image data and its position relative to the position of the imaging system is utilized by image guidance software to orient and position the image data to the patient's physical position in 3D space. In some embodiments, the reference frame is mounted at or near the area of the surgical procedure, with rigid mounting clamps or pins that allow for minimal adjustment of the reference frame's position. Procedures such as posterior cervical fixation, thoracolumbar cortical screw placement, and lumbosacral fixation may require the frame to be positioned in areas where instrument positions and trajectories potentially interfere with the reference frame. These interactions increase a risk of bumping the reference frame during the procedure or require temporary removal and reattachment of the reference frame, prompting another image acquisition and registration.

Embodiments herein describe adaptable reference frame mounts to provide surgeons multiple degrees of movement for positioning the reference frame relative to the surgical area of interest, reducing the potential of bumping the reference frame and the need for re-registration later in the procedure. Also described are methods of utilizing input from the reference frame mounts to a visual tracking system to adjust the position of the reference frame from one discrete pose to another discrete pose without the need for obtaining a new image and re-registering the reference frame. In some embodiments within the scope of this disclosure, the mounts include a first joint having first and second degrees of movement, a second joint having a third degree of movement, and a third joint having a fourth degree of movement. The first joint is a telescoping joint, the second joint is a sliding joint, and the third joint is a swivel joint. In certain embodiments, one or more of the joints includes discrete position features and indicia to allow adjustment of one or more joints between discrete positions and to allow a visual tracking system to determine the difference between the first and second discrete positions. In other embodiments, the second joint has a fifth degree of movement and is a ball-and-socket joint that is in axial alignment with the first joint. In some embodiments, the mount includes a clamp configured to couple the mount to a spinous process of a vertebra. In other embodiments, the mount includes a surface to support the reference frame.

In use, in embodiments within the scope of this disclosure, one or more of the joints is adjusted to a first discrete position disposing the reference frame in a first pose. The reference frame, in the first pose, is registered to a 3D image. The reference frame is disposed to a second pose by re-adjusting one or more of the joints to a second discrete position. The registered position of the reference frame relative to the 3D image is corrected by updating the position of the reference frame in the second pose based on the second discrete position of one or more of the joints. In some embodiments within the scope of this disclosure, a visual tracking system receives an input from the mount and the input is used to determine a positional difference between the first discrete position and the second discrete position of one or more of the joints. In other embodiments, the input indicating the change in position is user-entered into an image-guided surgery system.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Figure 2:
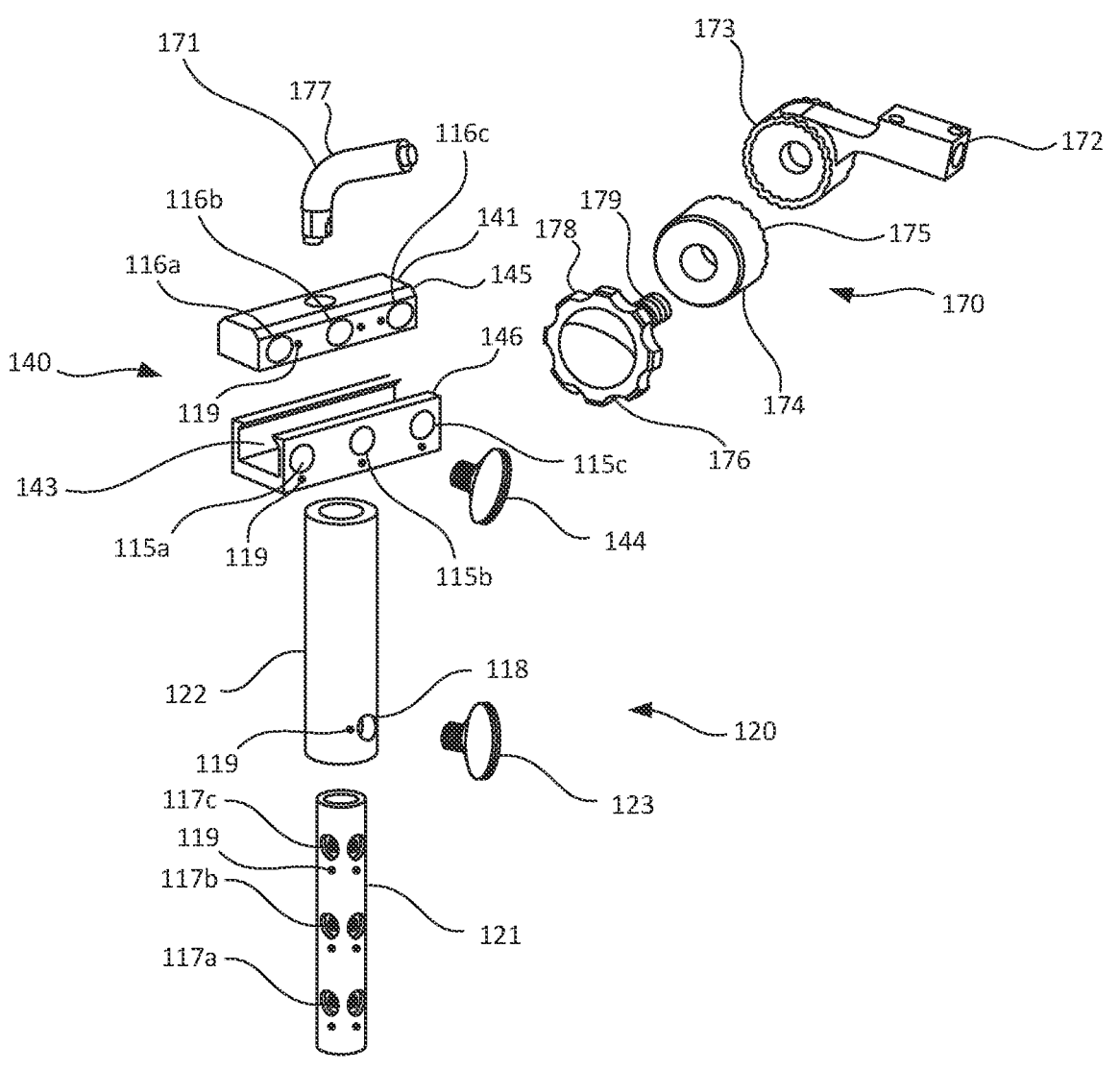
FIG. 2 is a perspective exploded view of the reference frame mount of FIG. 1.
Figure 3:
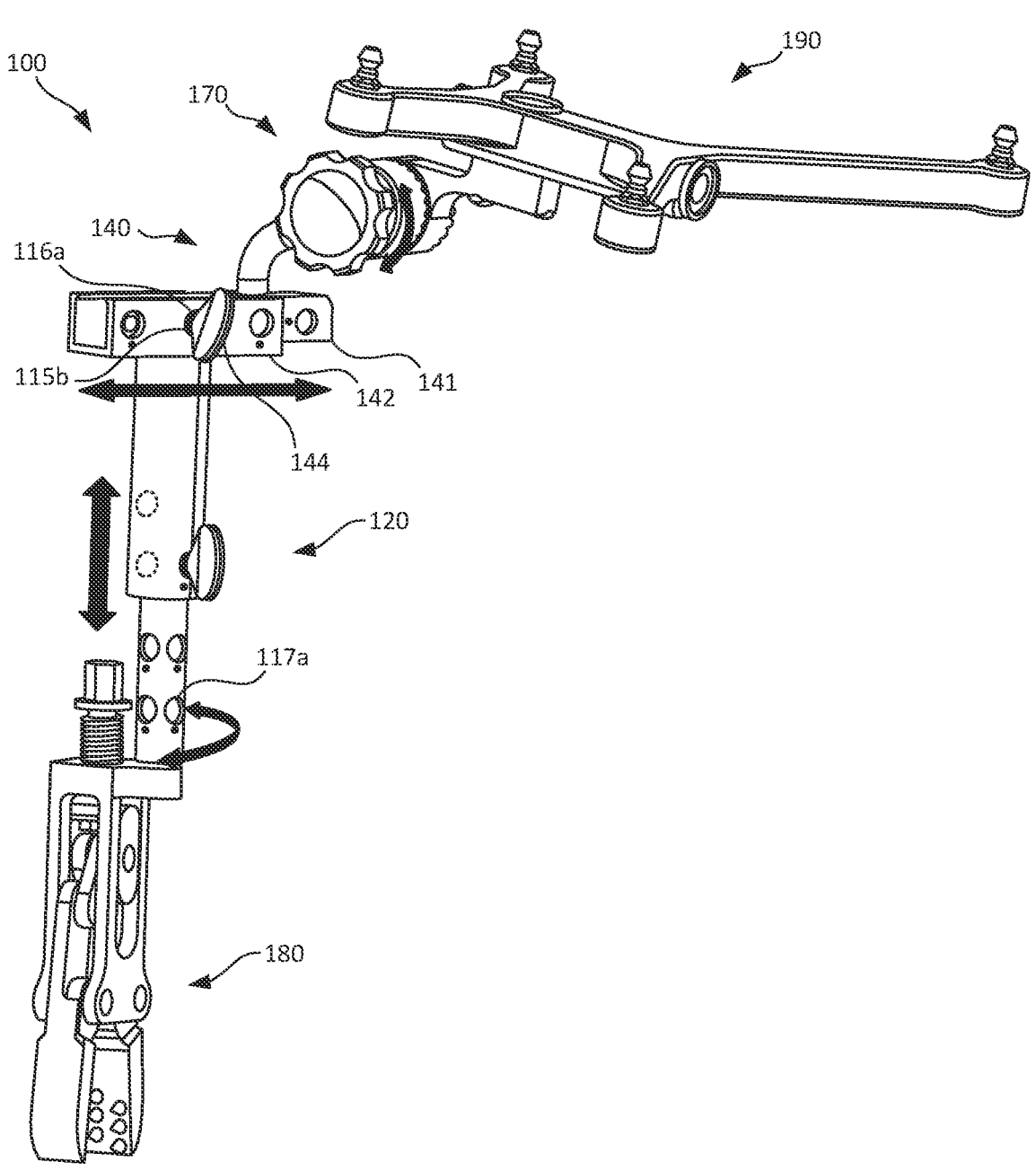
FIG. 3 is a perspective view of the reference frame mount of FIG. 1 in a discrete pose.
Figure 4:
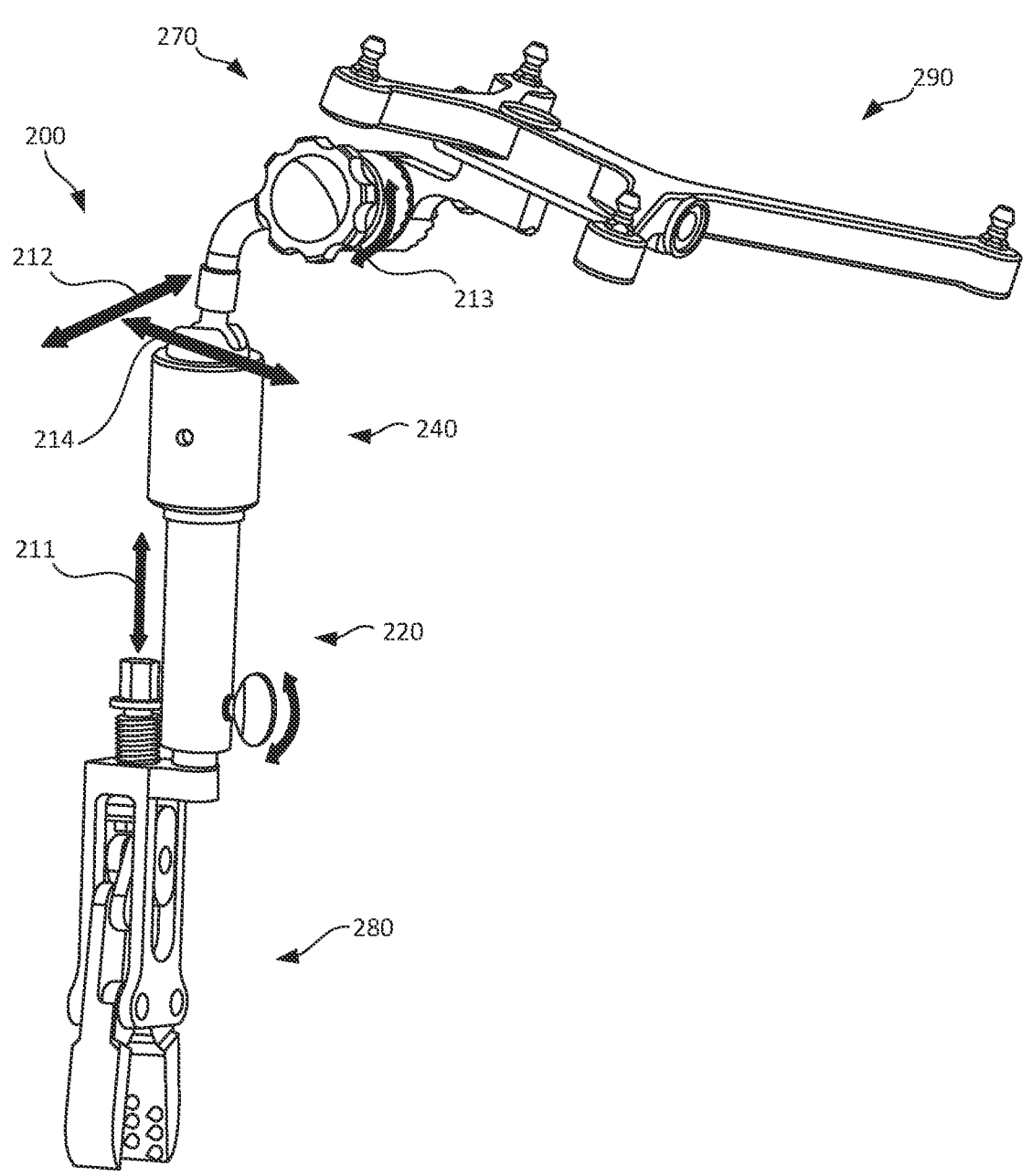
FIG. 4 is a perspective view of another embodiment of a reference frame mount.
Figure 5:
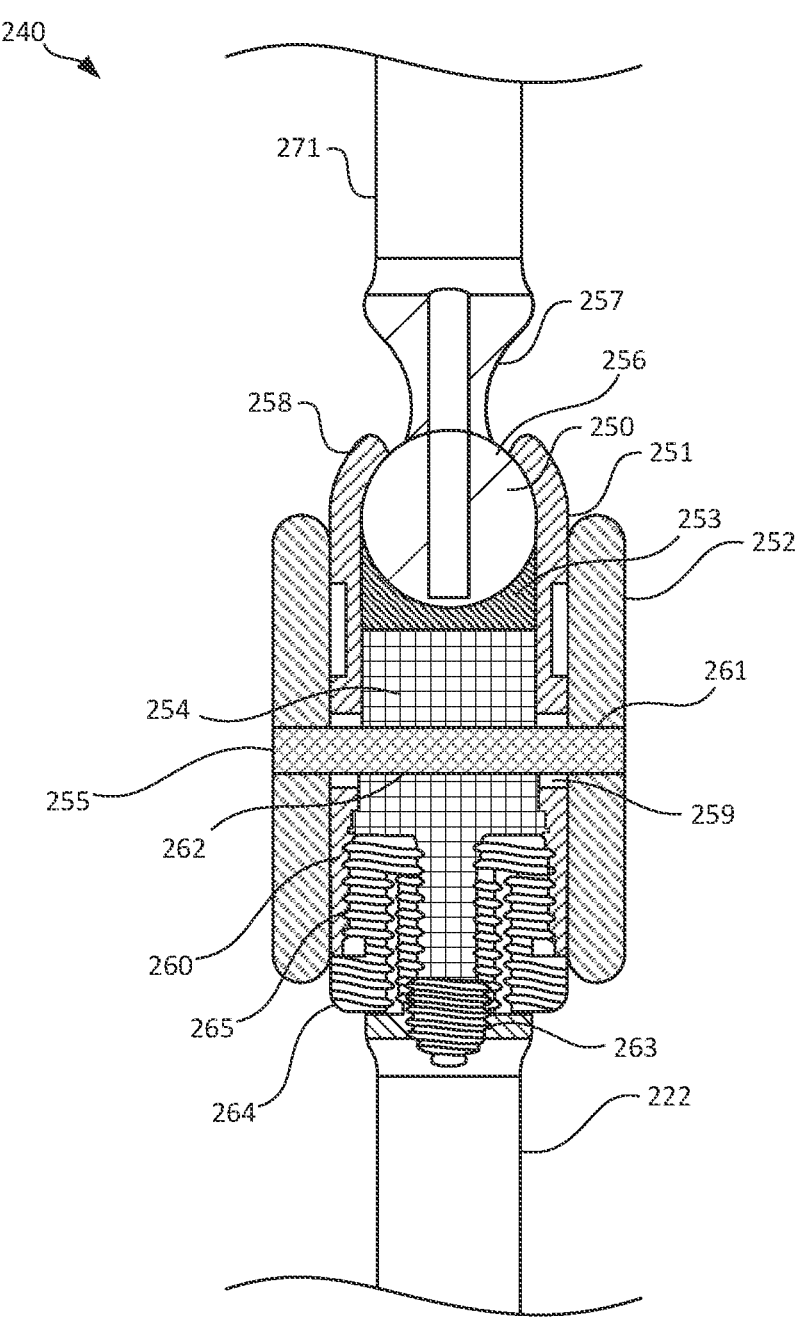
FIG. 5 is a cross-sectional view of a second joint of the reference frame mount of FIG. 4.
Figure 6:
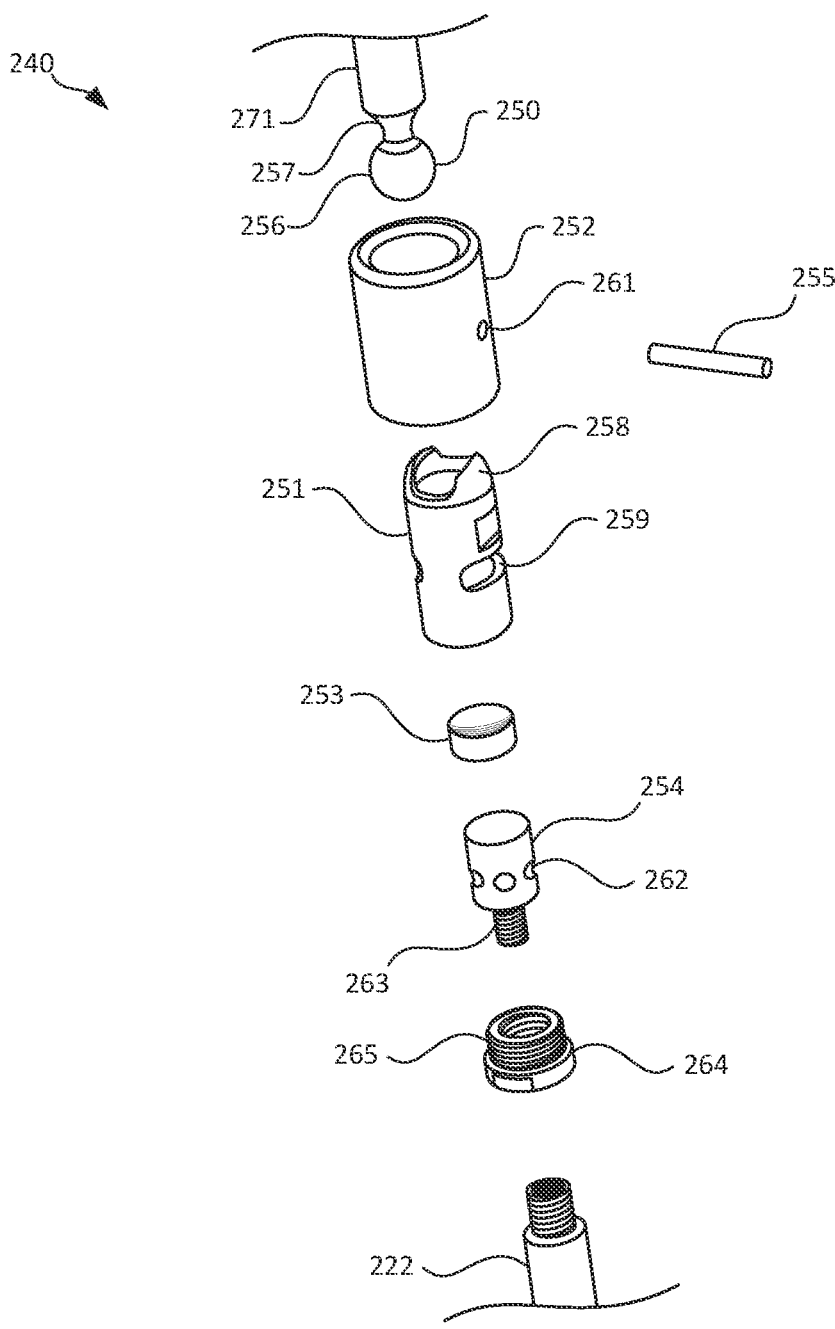
FIG. 6 is a perspective exploded view of the second joint of FIG. 5.
Figure 7A:
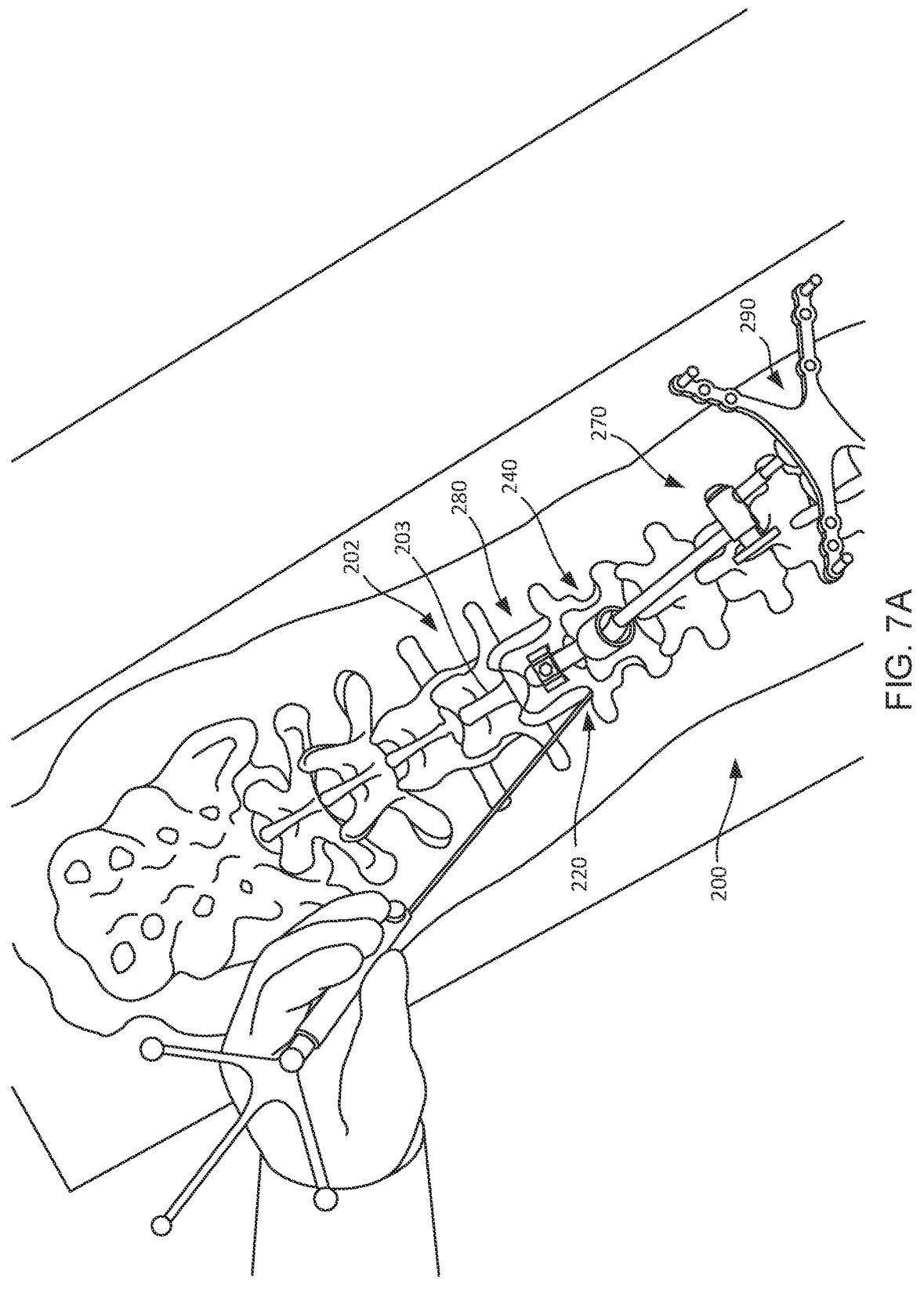
FIG. 7A is an overhead view of a surgical site where the reference frame mount of FIG. 4 is coupled to a spinous process of a patient and a reference frame is in a first pose.
Figure 7B:
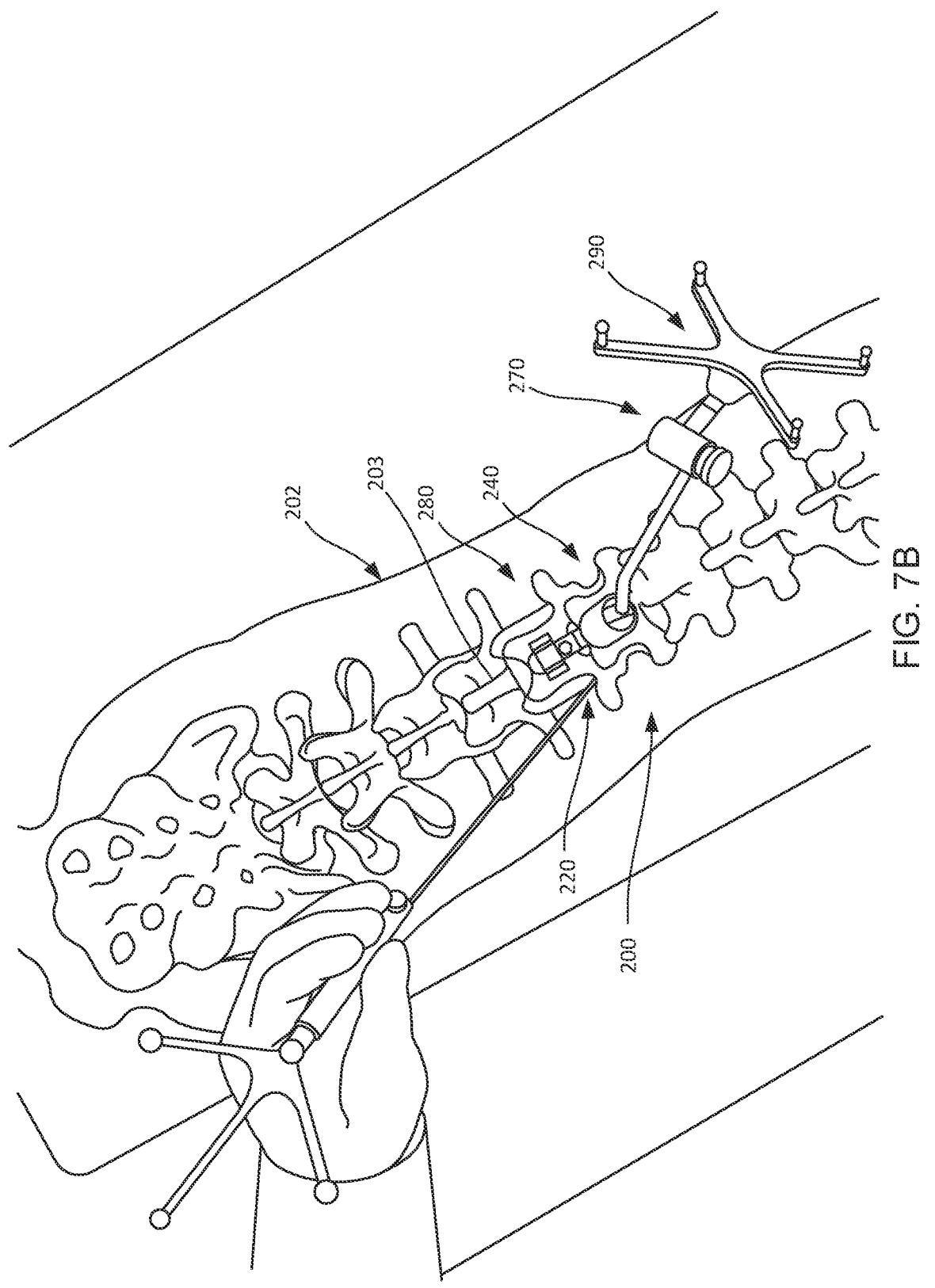
FIG. 7B is an overhead view of the surgical site where the reference frame mount of FIG. 4 is coupled to the spinous process of the patient and the reference frame is in the second pose.

FIGS. 1-3 illustrate an embodiment of a reference frame mount. FIGS. 4-6 illustrate another embodiment of a reference frame mount. FIG. 7A illustrates a surgical site where the reference frame mount of FIG. 4 is coupled to a spinous process of a patient and a reference frame is in a first pose. FIG. 7B illustrates the surgical site where the reference frame mount of FIG. 4 is coupled to the spinous process of the patient and the reference frame is in the second pose. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

As illustrated in FIGS. 1 and 2, an embodiment of a reference frame mount 100 includes a first joint 120, a second joint 140, a third joint 170, a clamp 180, and a reference frame support member 190. The first joint 120 is a telescoping joint that provides a first degree of freedom or axis of movement 111 and a second degree of freedom or axis of movement 110 to the reference frame mount 100. The first axis of movement 110 is axial movement along a longitudinal axis of the first joint 120. The first axis of movement 111 allows the reference frame mount 100 to be displaced vertically over a distance ranging from about 25 millimeters-45 millimeters. The second axis of movement 111 is a rotational movement about the longitudinal axis of the first joint 120. The second axis of movement 111 allows the reference frame mount 100 to be rotated about the longitudinal axis of the first joint 120. In some embodiments, the rotation may be 360 degrees in discrete increments of 90 degrees.

The first joint 120 includes an elongate shaft 121, an outer sleeve 122, and a locking mechanism 123. The shaft 121 can be formed as a cylinder or a rod of a rigid, non-magnetic material, such as stainless steel, titanium, or aluminum. Other materials are contemplated within the scope of this disclosure. A diameter of the shaft 121 may range from about 7 millimeters-10 millimeters and a length of the shaft 121 may range from about 3-5 centimeters. An end of the shaft 121 can be fixedly coupled to the clamp 180. The clamp 180 may be configured to couple the adaptable mount to a spinous process of a patient.

The outer sleeve 122 is slidably disposed over the shaft 121 and configured to be axially displaced relative to a longitudinal axis of the shaft 121. The outer sleeve 122 is formed as a cylinder having an inner diameter larger than the diameter of the shaft 121 to allow the outer sleeve 122 to be axially and rotationally displaced relative to the shaft 121. The outer sleeve 122 can be formed of the same material as the shaft 121. An end of the outer sleeve 122 is fixedly coupled to the second joint 140.

The locking mechanism 123 is coupled to the outer sleeve 122 and configured to prevent the outer sleeve 122 from being axially and rotationally displaced when actuated. As depicted in FIG. 1, the locking mechanism 123 may a thumb screw threadingly coupled to the outer sleeve 122 and configured to press an end against the shaft 121 when actuated. Other types of locking mechanisms are contemplated within the scope of this disclosure. For example, the locking mechanism 123 may be a clamp, a setscrew, a ball plunger, or a pull pin. As shown in FIGS. 1 and 2, the second joint 140 is a slide joint that provides a third degree of freedom or axis of movement 112 to the reference frame mount 100. The third axis of movement 112 is lateral movement along a longitudinal axis of the second joint 140 and perpendicular to the longitudinal axis of the first joint 120. In other words, the third axis of movement 112 allows a portion of the reference frame mount 100 to be radially displaced or offset from the longitudinal axis of the first joint 120. The reference mount 100 can be radially displace over functional angles ranging from 0 (vertical) to 90 degrees (horizontal).

The depicted second joint 140 includes an elongate rail 141, a socket portion 142, and a locking mechanism 144. The second joint 140 can be formed as of a rigid material, such as stainless steel, titanium, or aluminum. Other materials are contemplated within the scope of this disclosure. The rail 141 includes a generally rectangular cross-section shape with beveled top corners 145. Other shapes are contemplated. A length of the rail 141 may range from about 3-5 cm. A width of the rail 141 may range from about 12-20 mm. A height of the rail 141 can range from about 8-15 mm.

The socket portion 142 includes an elongate socket 143 sized to slidingly receive the rail 141. The socket 143 includes radial inwardly directed wall portions 146 configured to engage with the beveled top corners 145 of the rail 141 to prevent the rail 141 from vertical displacement from the socket 143. The locking mechanism 144 is coupled to the socket portion 142 and configured to prevent the rail 141 from being laterally or axially displaced along the longitudinal axis of the second joint 140 when actuated. As depicted in FIG. 1, the locking mechanism 144 may be a thumb screw threadingly coupled to the socket portion 142 and configured to press an end against the rail 141 when actuated. Other types of locking mechanisms are contemplated within the scope of this disclosure. For example, the locking mechanism 144 may be a clamp, a setscrew, a ball plunger, or a pull pin.

With continued reference to FIGS. 1 and 2, the third joint 170 is a rotational or starburst joint that provides a fourth degree of freedom or axis of movement 113 to the reference frame mount 100. The fourth axis of movement 113 is rotational movement about a horizontally oriented longitudinal axis of the third joint 170 in a single plane. In other words, the fourth axis of movement 113 allows the reference frame support member 190 to be displaced about the horizontally oriented longitudinal axis of the third joint 170 in a single plane of rotation. The reference frame support member 190 can rotationally displace over an arc distance ranging from 0 (vertical) to 90 degrees (horizontal) functionally.

The depicted third joint 170 includes a reference frame support 172, a locking cylinder 174, and a knob 176. The reference frame support member 190 is coupled to the reference frame support 172. The reference frame support 172 includes teeth 173 laid out in a circular pattern and extending laterally from both sides of the reference frame support 172. The locking cylinder 174 includes a cylindrical shape and locking teeth 175 extending from an end of the locking cylinder 174. The number of locking teeth 175 can be equivalent to the number of teeth 173. The locking teeth 175 can engage with the teeth 173 to lock the third joint 170 in a desired rotational position relative to a rotational axis of the third joint 170. A stem 171 is coupled to the locking cylinder 174 at a first end and the rail 141 of the second joint 140 at a second end. The stem 171 includes a bend 177 disposed between the first end and the second end. An angle of the bend 177 can range from about 30-60 degrees. The reference frame support 172 can be disposed on either side of the stem 171.

The knob 176 includes a handle 178 and a shaft 179. The shaft 179 extends from the handle 178 and includes threads disposed adjacent to a free end portion. The shaft 179 is disposed through the locking cylinder 174 and threadingly coupled to the reference frame support 172. The handle 178 can include grip features to facilitate rotation of the handle 178 by a hand of a user. The grip features can include recesses, bumps, grooves, contours, textured surfaces, and compliant surfaces. Other grip features are contemplated.

In use, the knob 176 is rotated in a first direction to unlock the third joint 170 wherein the reference frame support 172 is displaced away from the locking cylinder 174 allowing the locking teeth 175 to disengage from the teeth 173. The reference frame support 172 is rotated about the longitudinal axis of the third joint 170 to a desired position resulting in a desired reference frame pose. The knob 176 is rotated in a second direction to displace the reference frame support 172 toward the locking cylinder 174 causing the teeth 173 to mesh or engage with the locking teeth 175 and rotationally locking the third joint 170.

In certain embodiments, one or more of the first joint 120, the second joint 140, and the third joint 170 can include positioning features configured to allow the joints 120, 140, and 170 to be positioned in one or more discrete positions. The positioning features can include a detent comprising any one of a catch, a dog, a spring-operated-ball, and a pin. Other positioning features are contemplated within the scope of this disclosure. For example, as illustrated in FIGS. 1 and 2, the second joint 140 can comprise mating features 116*a-c* disposed on the rail 141 and corresponding mating positioning features 115*a-c* disposed on the socket 143. In use, the rail 141 can be positioned at any one of a plurality of discrete positions where any one of the mating positioning features 116*a-c* aligns with any one of the mating positioning features 115*a-c*. For example, as depicted in FIG. 1, the second joint 140 is in a first discrete position where the mating feature 116*c* is aligned with the mating feature 115*b* with the locking mechanism 144 disposed through the mating features 115*b*, 116*c*. In comparison, as illustrated in FIG. 3, the second joint 140 is laterally adjusted to a second discrete position where the mating feature 116*a* is aligned with the mating feature 115*b*. When the second joint 140 is adjusted from one discrete position to another discrete position, a registration of the reference frame support member 190 with the 3D patient image may be disturbed a known distance requiring a correction of the registration. The user may input the known distance between the discrete positions into the image-guided surgical system to correct the registration of the reference frame support member 190.

In some embodiments, one or more of the first joint 120, the second joint 140, and the third joint 170 can include visual indicia coupled to the positioning features. The indicia may include a light emitting diode (LED), a label, and a marking on the joint. Other indicia are contemplated. For example, as illustrated in FIG. 1, the visual indicia 119 are associated with each of the positioning features 115*a-c*, 116*a-c*, 117*a-c* of the second joint 140. When the second joint is adjusted from one discrete position to another discrete position, a visual tracking system of the image-guided surgical system can detect the indicia 119 at the discrete positions and automatically correct the reference frame registration for the difference in distance between the discrete positions.

FIGS. 4-7B depict an embodiment of a reference frame mount 200 that resembles the reference frame mount 100 described above in certain respects. Accordingly, like features are designated with like reference numerals, with the leading digit incremented to "2." For example, the embodiment depicted in FIGS. 4-7B includes a second joint 240 that may, in some respects, resemble the second joint 140 of FIG. 1. Relevant disclosure set forth above regarding similarly identified features thus may not be repeated hereafter. Moreover, specific features of the reference frame mount 100 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the reference frame mount 200 and related components depicted in FIGS. 4-7B. Any suitable combination of the features, and variations of the same, described with respect to the reference frame mount 100 and related components illustrated in FIG. 1 can be employed with the reference frame mount 200 and related components of FIGS. 4-7B, and vice versa. This pattern of disclosure applies equally to further embodiments depicted in subsequent figures and described hereafter, wherein the leading digits may be further incremented.

FIG. 4 illustrates an embodiment of a reference frame mount 200. As illustrated in FIG. 4, the reference frame mount 200 includes a first joint 220, a third joint 270, a clamp 280, and a reference frame support member 290 that substantially resemble the first joint 120, the third joint 170, the clamp 180, and the reference frame support member 190, respectively, of the reference frame mount 100 as previously described. FIG. 4 further illustrates a second joint 240. The second joint 240 is a swivel or ball-and-socket joint that provides a third degree of freedom or axis of movement 213 and a fifth degree of freedom or axis of movement 214 to the reference frame mount 200. The third axis of movement 213 is lateral or side-to-side movement along a laterally oriented transverse axis of the second joint 240. In other words, the third axis of movement 213 allows a portion of the reference frame mount 200 to be laterally displaced or offset from the longitudinal axis of the second joint 240. A portion of the reference frame mount 200 can be laterally displaced over an arc length ranging from about 0 to 90 degrees functionally. The fifth axis of movement is forward-to-backward movement along a forward-to-backward oriented transverse axis of the second joint 240. The fifth axis of movement 214 allows the portion of the reference frame mount 200 to be displaced forward or backward of the longitudinal axis of the second joint 240. The portion of the reference frame mount 200 may be displaced forward-to-backward over an arc length ranging from about −135 degrees to about 135 degrees from vertical. The second joint 240 is in axial alignment with the first joint 220.

As illustrated in FIGS. 5 and 6, the illustrated second joint 240 includes a ball portion 250, a socket portion 251, an outer sleeve 252, a ball seat 253, a piston 254, a pin 255, and a threaded nut 264. The components of the second joint 240 can be formed from a rigid material, such as stainless steel, titanium, or aluminum. Other materials are contemplated within the scope of this disclosure. The ball portion 250 includes a ball 256 and a stem 257 coupled to and extending away from the ball 256. A diameter of the ball 256 can range from about 8-12 mm. The socket portion 251 is sized to receive the ball 256 at a proximal end. The proximal end is partially closed with retention flanges 258 conforming to the ball 256 and extending beyond an equator of the ball 256, wherein the ball 256 is retained within the socket portion 251 by the retention flanges 258. The socket portion 251 further comprises a pin slot 259 oriented along a transverse axis of the socket portion 251 and configured to receive the pin 255. A width of the pin slot 259 is larger than a diameter of the pin 255. Internal threads 260 are disposed at a distal end of the socket portion 251.

The outer sleeve 252 is disposed over and configured to rotate about the socket portion 251. The outer sleeve 252 includes a cylindrical shape with open proximal and distal ends. Pin ports 261 are disposed in a wall of the outer sleeve 252. The pin ports 261 are configured to receive the pin 255. The piston 254 is slidingly disposed within the socket portion 251. The piston 254 is disposed distally of the ball portion 250 with a ball seat 253 disposed between the ball portion 250 and the piston 254. Pin passages 262 are disposed through the piston 254 and configured to receive the pin 255. As shown in FIG. 5, the pin 255 is disposed through the pin ports 261 of the outer sleeve 252, the pin slot 259 of the socket portion 251, and the pin passages 262 of the piston 254. The pin 255 is configured to operatively couple the outer sleeve 252 with the socket portion 251 and the piston 254. The piston 254 includes a threaded portion 263 to couple the piston 254 to the outer sleeve 222 of the first joint 220. The threaded nut 264 is disposed distally of the piston 254 and is coupled to the outer sleeve 222. The nut 264 includes external threads 265 configured to engage with the internal threads 260 of the socket portion 251. The ball seat 253 is generally disk shaped with a concave upper surface that is shaped to substantially match the contour of the ball portion 250. The ball seat 253 may be formed of a compressible material, such as Teflon, polyethylene, polyurethane, or Delrin. The ball seat 253 may be a low friction material. For example, the ball seat 253 may be metal (e.g., stainless, titanium, or aluminum) with diamond like carbon coatings or gall tough metals such as nitronic 60 or low friction polymers such as Ultra-high-molecular-weight polyethylene (UHMWPE). Other materials are contemplated.

The second joint 240 is in axial alignment with the first joint 220. In other words, the components of the second joint 240 are axially aligned with the first joint 220 wherein the components do not extend substantially radially outward from the longitudinal axis of the first joint 220. This embodiment of the second joint 240, prevents the components from interfering with instruments used during a surgical procedure and prevents the components from being bumped by a user and resulting in displacement of the reference frame and a need to re-register the reference frame pose.

The second joint 240 is configured to be transitioned from an unlocked state to a locked state. In the unlocked state, the second joint 240 is freely adjustable. In other words, when the second joint 240 is in the unlocked state, the second joint 240 can be freely adjusted in the third axis of movement 212 and/or the fifth axis of movement 214 as previously described. In the locked state, the second joint 240 is prevented from being inadvertently displaced. In other words, when the second joint 240 is in the locked state, the second joint 240 is prevented from being inadvertently displaced in the third axis of movement 212 and/or the fifth axis of movement 214. When the second joint 240 is inadvertently displaced, the reference frame pose is altered, resulting in a need to re-register the reference frame pose.

When the second joint 240 is in the unlocked state, the outer sleeve 252 is rotated in a first direction (e.g., counterclockwise) as the internal threads 260 of the socket portion 251 engage with the external threads 265 of the nut 264. When the outer sleeve 252 is rotated in the first direction, the pin 255 is rotated within the pin slot 259 and the piston 254 is rotated relative to the socket portion 251. The pin slot 259 can restrain rotation of the outer sleeve 252, piston 254, and pin 255 from about 0 degrees to about 80 degrees. As the threads 260, 265 threadingly engage, the socket portion 251 is displaced distally causing the pin 255 to be displaced distally within the pin slot 259. When the pin 255 is displaced distally, the outer sleeve 252 and the piston 254 are displaced distally relative to the socket portion 251. When the piston 254 is displaced distally, the ball seat 253 is allowed to move distally to substantially release contact with the ball portion 250 allowing the ball portion 250 to be freely moved in the third and fifth axes of movement 212, 214.

When the second joint 240 is in the locked state, the outer sleeve 252 is rotated in a second direction (e.g., clockwise) as the internal threads 260 of the socket portion 251 engage with the external threads 265 of the nut 264. When the outer sleeve 252 is rotated in the second direction, the pin 255 is rotated within the pin slot 259 and the piston 254 is rotated relative to the socket portion 251. As the threads 260, 265 threadingly engage, the socket portion 251 is displaced proximally causing the pin 255 to be displaced proximally within the pin slot 259. When the pin 255 is displaced proximally, the outer sleeve 252 and the piston 254 are displaced proximally relative to the socket portion 251. When the piston 254 is displaced proximally, the ball seat 253 is displaced proximally to engage with or press against the ball portion 250 causing the ball portion 250 to be locked in a position and prevented from movement in the third and fifth axes of movement 212, 214 by a frictional force between the ball portion 250 and the ball seat 253.

FIGS. 7A and 7B illustrate the reference frame mount 200 in use. As depicted in FIG. 7A, the reference frame mount 200 is coupled to a spinous process 203 of a patient's spine 202 utilizing the clamp 280. The first, second, and third joints 220, 240, 270 are disposed in first discrete positions resulting in the reference frame mount 200 being disposed in a first pose wherein the reference frame support member 290 and a reference frame are disposed at a first discrete position relative to the patient's spine 202. The first discrete positions of one or more of the joints 220, 240, 270 may be used as input to a surgical tracking system to register the reference frame coupled to the reference frame support member to a 3D patient image. In some embodiments, an indicium disposed in a first discrete position in the first pose can be used by a surgical tracking system to register the reference frame to a 3D patient image.

As depicted in FIG. 7B, the reference frame mount 200 is adjusted at the second joint 240 to a second discrete position to displace the reference frame support member 290 and the reference frame relative to the patient's spine 202 resulting in the reference frame mount 200 disposed in a second pose. In other embodiments, the reference frame mount 200 may be adjusted at one or more of the joints 220, 240, 270. The second discrete position of the second joint 240 can be used as input to a surgical tracking system to correct the registration of the reference frame with the 3D patient image. In other embodiments, a second discrete position of one or more of the joints 220, 240, 270 may be used as input to correct the registration of the reference frame with the 3D patient image. In some embodiments, the visual indicium is displaced from the first discrete position to a second discrete position in the second pose. In the second discrete position, the indicium can be used to correct the registration of the reference frame to the 3D patient image.

Any methods disclosed herein comprise one or more steps or actions for performing the described method. The method steps and/or actions may be interchanged with one another.

In other words, unless a specific order of steps or actions is required for proper operation of the embodiment, the order and/or use of specific steps and/or actions may be modified. For example, a method of correcting a registration of a reference frame for image-guided spinal surgery may include one or more of the following steps: adjusting a position of one or more of a first joint, a second joint, and a third joint of a reference frame mount to a first discrete position; registering the reference frame in a first pose relative to a patient landmark of a first 3D image; re-adjusting the reference frame to a second pose by adjusting a position of one or more of the first joint, the second joint, and the third joint to a second discrete position; and correcting a position of the reference frame captured in registering the reference frame by updating a position of the reference frame to the second pose based on the second discrete position of one or more of the first joint, the second joint, and the third joint. Other steps are also contemplated.

For one or more embodiments, at least one of the components set forth in one or more of the preceding figures may be configured to perform one or more operations, techniques, processes, and/or methods as set forth in the Example Section below.

EXAMPLE SECTION

The following Examples pertain to further embodiments.

Example 1 may include an adaptable mount for a reference frame for image-guided spinal surgery, comprising: a first joint comprising: a first axis of movement configured to position the reference frame vertically relative to a longitudinal axis of the first joint; and a second axis of movement configured to position the reference frame rotationally relative to the longitudinal axis of the first joint; a second joint comprising a third axis of movement configured to position the reference frame laterally relative to the longitudinal axis of the first joint; and a third joint comprising a fourth axis of movement configured to position the reference frame rotationally relative to a rotational axis of the third joint; wherein one or more of the first joint, the second joint, and the third joint further comprise positioning features configured to position the reference frame in discrete poses.

Example 2 may include the adaptable mount of Example 1, wherein the first joint further comprises a telescoping joint.

Example 3 may include the adaptable mount of Example 1, wherein the first joint further comprises: an elongate shaft; an outer sleeve slidably disposed over the elongate shaft, and a locking mechanism configured to lock the outer sleeve in a vertical position relative to the shaft.

Example 4 may include the adaptable mount of Example 3, wherein the second joint is coupled to the elongate shaft.

Example 5 may include the adaptable mount of Example 1, wherein the second joint further comprises a sliding joint.

Example 6 may include the adaptable mount of Example 1, wherein the second joint further comprises: an elongate rail; a socket portion configured to slidably receive the rail; and a locking mechanism configured to lock the rail in a lateral position relative to the socket portion.

Example 7 may include the adaptable mount of Example 1, wherein the second joint comprises a fifth axis of movement and is configured to position the reference frame forward of or back of a longitudinal axis of the second joint.

Example 8 may include the adaptable mount of Example 1, wherein the second joint is axially aligned with the first joint.

Example 9 may include the adaptable mount of Example 1, wherein the second joint further comprises a ball-and-socket joint.

Example 10 may include the adaptable mount of Example 1, wherein the second joint further comprises: a ball portion; a socket portion configured to receive the ball portion; an outer sleeve rotatable relative to the socket portion; a ball seat configured to engage with the ball portion; and a piston configured to compress the ball seat against the ball portion, wherein the ball portion is locked in a position relative to the socket portion when the ball seat is compressed against the ball portion.

Example 11 may include the adaptable mount of Example 1, wherein the third joint further comprises a swivel joint configured to allow displacement of the reference frame in a single plane.

Example 12 may include the adaptable mount of Example 1, wherein the third joint further comprises: a stem coupled to the second joint at a first end; a locking cylinder comprising a first plurality of teeth and coupled to the stem at a second end; a reference frame support comprising a second plurality of teeth; and a knob configured to press the first plate against the second plate, wherein the first plurality of teeth are configured to mesh with the second plurality of teeth to lock the third joint in a position relative to a rotational axis of the third joint.

Example 13 may include the adaptable mount of Example 1, wherein the positioning features comprise a detent comprising any one of a catch, a dog, a spring-operated-ball, a pin, and any combination thereof.

Example 14 may include the adaptable mount of Example 1, further comprising indicia configured to visually indicate a position of one or more of the first joint, the second joint, and the third joint.

Example 15 may include the adaptable mount of Example 14, wherein the indicia comprise any one of a light emitting diode (LED), a label, a marking, and any combination thereof.

Example 16 may include the adaptable mount of Example 1, further comprising a clamp coupled to the first joint and configured to couple the adaptable mount to a spinous process of a patient.

Example 17 may include an adaptable mount for a reference frame for image-guided spinal surgery, comprising: a first joint comprising: a first axis of movement configured to position the reference frame vertically relative to a longitudinal axis of the first joint; and a second axis of movement configured to position the reference frame rotationally relative to the longitudinal axis of the first joint; a second joint comprising: a third axis of movement configured to position the reference frame laterally relative to the longitudinal axis of the first joint; an elongate rail; a socket portion configured to slidably receive the rail; and a first locking mechanism configured to lock the rail in a lateral position relative to the socket portion; and positioning features configured to position the reference frame in discrete poses; and a third joint comprising a fourth axis of movement configured to position the reference frame rotationally relative to a rotational axis of the third joint.

Example 18 may include the adaptable mount of Example 17, wherein the first joint further comprises a telescoping joint.

Example 19 may include the adaptable mount of Example 17, wherein the first joint further comprises: an elongate shaft; an outer sleeve slidably disposed over the elongate shaft; and a second locking mechanism configured to lock the outer sleeve in a vertical position relative to the shaft.

Example 20 may include the adaptable mount of Example 19, wherein the second joint is coupled to an end of the shaft.

Example 21 may include the adaptable mount of Example 17, wherein the second joint further comprises a sliding joint.

Example 22 may include the adaptable mount of Example 17, wherein the third joint further comprises a swivel joint configured to allow displacement of the reference frame in a single plane.

Example 23 may include the adaptable mount of Example 17, wherein the third joint further comprises: an arm coupled to the second joint at a first end; a first plate comprising a first plurality of teeth and coupled to the arm at a second end; a second plate comprising a second plurality of teeth and coupled to a reference frame support; and a knob configured to press the first plate against the second plate, wherein the first plurality of teeth are configured to mesh with the second plurality of teeth to lock the third joint in a position relative to the arm.

Example 24 may include the adaptable mount of Example 17, wherein the positioning features comprise a detent comprising any one of a catch, a dog, a spring-operated-ball, a pin, and any combination thereof.

Example 25 may include the adaptable mount of Example 17, wherein the second joint further comprises indicia configured to visually indicate a position of one or more of the first joint, the second joint, and the third joint.

Example 26 may include the adaptable mount of Example 25, wherein the indicia comprise any one of a light emitting diode (LED), a label, a marking, and any combination thereof.

Example 27 may include the adaptable mount of Example 17, further comprising a clamp coupled to the first joint and configured to couple the adaptable mount to a spinous process of a patient.

Example 28 may include an adaptable mount for a reference frame for image-guided spinal surgery, comprising: a first joint comprising: a first axis of movement configured to position the reference frame vertically relative to a longitudinal axis of the first joint; and a second axis of movement configured to position the reference frame rotationally relative to the longitudinal axis of the first joint; a second joint comprising a third axis of movement configured to position the reference frame laterally relative to the longitudinal axis of the first joint, wherein the second joint is in axial alignment with the first joint; and a third joint comprising a fourth axis of movement configured to position the reference frame rotationally relative to a rotational axis of the third joint.

Example 29 may include the adaptable mount of Example 28, wherein the first joint further comprises a telescoping joint.

Example 30 may include the adaptable mount of Example 28, wherein the first joint further comprises: an elongate shaft; an outer sleeve slidably disposed over the elongate shaft; and a locking mechanism configured to lock the outer sleeve in a vertical position relative to the shaft.

Example 31 may include the adaptable mount of Example 30, wherein the second joint is coupled to an end of the shaft.

Example 32 may include the adaptable mount of Example 28, wherein the second joint comprises a fifth axis of movement and is configured to position the reference frame forward of or back of a longitudinal axis of the second joint.

Example 33 may include the adaptable mount of Example 28, wherein the second joint further comprises a ball-and-socket joint.

Example 34 may include the adaptable mount of Example 28, wherein the second joint further comprises: a ball portion; a socket portion configured to receive the ball portion; an outer sleeve rotatable relative to the socket portion; a ball seat configured to engage with the ball portion; and a piston configured to compress the ball seat against the ball portion, wherein the ball portion is locked in a position relative to the socket portion when the ball seat is compressed against the ball portion.

Example 35 may include the adaptable mount of Example 28, wherein the third joint further comprises a swivel joint configured to allow displacement of the reference frame in a single plane.

Example 36 may include the adaptable mount of Example 28, wherein the third joint further comprises: an arm coupled to the second joint at a first end; a first plate comprising a first plurality of teeth and coupled to the arm at a second end; a second plate comprising a second plurality of teeth and coupled to a reference frame support; and a knob configured to press the first plate against the second plate, wherein the first plurality of teeth are configured to mesh with the second plurality of teeth to lock the third joint in a position relative to the arm.

Example 37 may include the adaptable mount of Example 28, further comprising a clamp coupled to the first joint and configured to couple the adaptable mount to a spinous process of a patient.

Example 38 may include a method of correcting a registration of a reference frame for image-guided spinal surgery, comprising: adjusting a position of one or more of a first joint, a second joint, and a third joint of a reference frame mount to a first discrete position; registering the reference frame in a first pose relative to a patient landmark of a first three-dimensional (3D) image; re-adjusting the reference frame to a second pose by adjusting the position of one or more of the first joint, the second joint, and the third joint to a second discrete position; and correcting a position of the reference frame captured in registering the reference frame by updating a position of the reference frame to the second pose based on the second discrete position of one or more of the first joint, the second joint, and the third joint.

Example 39 may include the method of Example 38, further comprising using a visual tracking system to determine a difference between the first discrete position and the second discrete position of one or more of the first joint, the second joint, and the third joint.

Example 40 may include the method of Example 38, wherein the reference frame mount comprises indicia configured to indicate a position of one or more of the first joint, the second joint, and the third joint.

Example 41 may include the method of Example 40, further comprising receiving an input indicating a discrete position of one or more of the first joint, the second joint, and the third joint.

Example 42 may include the method of Example 41, wherein the input is user-entered into an image-guided surgery system.

Example 43 may include the method of Example 40, wherein the indicia comprise any one of a light emitting diode (LED), a label, a marking, and any combination thereof.

Reference throughout this specification to "an embodiment" or "the embodiment" means that a particular feature, structure, or characteristic described in connection with that embodiment is included in at least one embodiment. Thus, the quoted phrases, or variations thereof, as recited through-out this specification are not necessarily all referring to the same embodiment.

Similarly, in the above description of embodiments, vari-ous features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The phrases "coupled to" and "in communication with" refer to any form of interaction between two or more entities, including mechanical, electrical, magnetic, electro-magnetic, fluid, and thermal interaction. Two components may be coupled to or in communication with each other even though they are not in direct contact with each other. For example, two components may be coupled to or in commu-nication with each other through an intermediate compo-nent.

The directional terms "distal" and "proximal" are given their ordinary meaning in the art. That is, the distal end of a medical device means the end of the device furthest from the practitioner during use. The proximal end refers to the opposite end, or the end nearest to the practitioner during use.

References to approximations are made throughout this specification, such as by use of the term "substantially." For each such reference, it is to be understood that, in some embodiments, the value, feature, or characteristic may be specified without approximation. For example, where quali-fiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a housing having "a stopper," the disclosure also contemplates that the housing can have two or more stop-pers.

Unless otherwise stated, all ranges include both endpoints and all numbers between the endpoints.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the invention.

The claims following this written disclosure are hereby expressly incorporated into the present written disclosure, with each claim standing on its own as a separate embodi-ment. This disclosure includes all permutations of the inde-pendent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An adaptable reference frame mount for supporting a reference frame for image-guided spinal surgery, compris-ing:
    a first joint comprising:
        an elongated shaft;
        an outer sleeve slidably disposed over the elongated shaft;
        a locking mechanism configured to lock the outer sleeve in a vertical position relative to the shaft;
        a first axis of movement configured to position the reference frame vertically relative to a longitudinal axis of the first joint; and
        a second axis of movement configured to position the reference frame rotationally relative to the longitu-dinal axis of the first joint;
    a second joint comprising a third axis of movement configured to position the reference frame laterally relative to the longitudinal axis of the first joint; and
    a third joint comprising a fourth axis of movement configured to position the reference frame rotationally relative to a rotational axis of the third joint;
    wherein one or more of the first joint, the second joint, and the third joint further comprise positioning features configured to position the reference frame in discrete poses.

2. The adaptable mount of claim 1, wherein the second joint further comprises:
    an elongate rail;
    a socket portion configured to slidably receive the rail; and
    a locking mechanism configured to lock the rail in a lateral position relative to the socket portion.

3. The adaptable mount of claim 1, wherein the second joint further comprises a fifth axis of movement and is configured to position the reference frame forward of or back of a longitudinal axis of the second joint.

4. The adaptable mount of claim 1, wherein the second joint further comprises:
    a ball portion;
    a socket portion configured to receive the ball portion;
    an outer sleeve rotatable relative to the socket portion;
    a ball seat configured to engage with the ball portion; and
    a piston configured to compress the ball seat against the ball portion,
    wherein the ball portion is locked in a position relative to the socket portion when the ball seat is compressed against the ball portion.

5. The adaptable mount of claim 1, wherein the third joint further comprises:
    a stem coupled to the second joint at a first end;

15 a locking cylinder comprising a first plate comprising a first plurality of teeth and coupled to the stem at a second end;

a reference frame support comprising a second plate comprising a second plurality of teeth; and a knob configured to press the first plate against the second plate, wherein the first plurality of teeth are configured to mesh with the second plurality of teeth to lock the third joint in a position relative to a rotational axis of the third joint.

6. The adaptable mount of claim 1, further comprising indicia configured to visually indicate a position of one or more of the first joint, the second joint, and the third joint.

7. The adaptable mount of claim 6 wherein the indicia comprise any one of a light emitting diode (LED), a label, a marking, and any combination thereof.

8. The adaptable mount of claim 1, further comprising a clamp coupled to the first joint and configured to couple the adaptable mount to a spinous process of a patient.

9. The adaptable mount of claim 1, wherein the first joint comprises a telescoping joint.

10. The adaptable mount of claim 1, wherein the second joint comprises a sliding joint.

11. An adaptable reference frame mount for supporting a reference frame for image-guided spinal surgery, comprising:

a telescoping first joint comprising:

a first axis of movement configured to position the reference frame vertically relative to a longitudinal axis of the first joint; and a second axis of movement configured to position the reference frame rotationally relative to the longitudinal axis of the first joint;

a second joint comprising a third axis of movement configured to position the reference frame laterally relative to the longitudinal axis of the first joint, wherein the second joint is in axial alignment with the first joint; and a third joint comprising a fourth axis of movement configured to position the reference frame rotationally relative to a rotational axis of the third joint.

12. The adaptable mount of claim 11, wherein the second joint comprises a fifth axis of movement and is configured to position the reference frame forward of or back of a longitudinal axis of the second joint.

13. The adaptable mount of claim 11, wherein the second joint further comprises a ball-and-socket joint.

14. The adaptable mount of claim 11, wherein the third joint further comprises a swivel joint configured to allow displacement of the reference frame in a single plane.

15. The adaptable mount of claim 11, further comprising a clamp coupled to the first joint and configured to couple the adaptable mount to a spinous process of a patient.

16. An adaptable reference frame mount for supporting a reference frame for image-guided spinal surgery, comprising:

a first joint comprising:

a first axis of movement configured to position the reference frame vertically relative to a longitudinal axis of the first joint; and a second axis of movement configured to position the reference frame rotationally relative to the longitudinal axis of the first joint;

a second joint comprising:

a third axis of movement configured to position the reference frame laterally relative to the longitudinal axis of the first joint;

an elongate rail;

a socket portion configured to slidably receive the rail; and a first locking mechanism configured to lock the rail in a lateral position relative to the socket portion; and positioning features configured to position the reference frame in discrete poses; and a third joint comprising a fourth axis of movement configured to position the reference frame rotationally relative to a rotational axis of the third joint.

17. The adaptable mount of claim 16, wherein the first joint comprises a telescoping joint.

18. The adaptable mount of claim 16, wherein the first joint further comprises:

an elongate shaft;

an outer sleeve slidably disposed over the elongate shaft; and a second locking mechanism configured to lock the outer sleeve in a vertical position relative to the shaft.

19. The adaptable mount of claim 16, wherein the third joint further comprises:

an arm coupled to the second joint at a first end;

a first locking cylinder comprising a first plurality of teeth and coupled to the arm at a second end;

a second locking cylinder comprising a second plurality of teeth and coupled to a reference frame support; and a knob configured to press the first locking cylinder against the second plate second locking cylinder, wherein the first plurality of teeth are configured to mesh with the second plurality of teeth to lock the third joint in a position relative to the arm.

* * * * *